United States Patent [19]
Martinotti

[11] Patent Number: 5,766,175
[45] Date of Patent: Jun. 16, 1998

[54] RETINACULUM FOR ORTHOPEDIC TRAUMATOLOGY

[76] Inventor: Lucio Martinotti, Via Mauro Macchi, 65, 20124 Milan, Italy

[21] Appl. No.: 559,020

[22] Filed: Nov. 16, 1995

[30] Foreign Application Priority Data

Nov. 22, 1994 [IT] Italy .................. 94A002365

[51] Int. Cl.$^6$ .................................. A61B 17/80
[52] U.S. Cl. .................................. 606/69
[58] Field of Search .................. 606/69, 70, 71, 606/61, 60, 72, 73, 74, 101

[56] References Cited

U.S. PATENT DOCUMENTS

| | | | |
|---|---|---|---|
| 5,015,248 | 5/1991 | Burstein et al. | 660/74 |
| 5,180,381 | 1/1993 | Aust et al. | 606/61 |
| 5,201,737 | 4/1993 | Leibinger et al. | 606/69 |
| 5,527,311 | 6/1996 | Proctor et al. | 606/61 |
| 5,586,985 | 12/1996 | Putnam et al. | 606/69 |

FOREIGN PATENT DOCUMENTS

| | | |
|---|---|---|
| 2 466 977 | 10/1979 | France. |
| 90 10 051.4 | 7/1990 | Germany. |
| 91 14 118.4 | 11/1991 | Germany. |
| 91 15 341.7 | 12/1991 | Germany. |
| 611 147 | 1/1977 | Switzerland. |

*Primary Examiner*—Guy V. Tucker
*Attorney, Agent, or Firm*—Collard & Roe, P.C.

[57] ABSTRACT

A device for securing fractured bone segments in place including a planar retinaculum having a series of apertures extending therethrough. The apertures are divided into three separate groups, with each group having a different diameter. The diameters range between 2.0 mm and 6.5 mm. The retinaculum has a thickness in the range of 0.5 mm to 2.0 mm. A thumb tack extends through the smallest aperture to removably secure fractured bone segments to the retinaculum. The apertures are arranged along the retinaculum in a repeating pattern. The retinaculum may be used in conjunction of a bone plate made from the same material.

7 Claims, 6 Drawing Sheets

RETINACULUM FOR ORTHOPEDIC TRAUMATOLOGY

BACKGROUND OF THE INVENTION

1. Field of the Invention

The invention relates to a retinaculum used for orthopedic traumatology. More particularly, it relates to a retinaculum which can be used in a wide variety of bone fractures.

2. The Prior Art

Known reticula have been used primarily in maxillofacial surgery. However, they are generally unsuitable for use in orthopedic traumatology because of the thicknesses and the configuration of the perforations.

SUMMARY OF THE INVENTION

Accordingly, it is an object of the present invention to provide a retinaculum particularly adapted for orthopedic traumatology.

It is a further object of the present invention to provide a retinaculum with a series of holes of different diameters which is temporarily attached to a fractured bone with nails or thumb tacks.

These and other related objects are achieved according to the invention by a device for securing fractured bone segments in place comprising a planar retinaculum having a plurality of apertures extending therethrough. The apertures are of three or more different diameters ranging from 2 mm to 6.5 mm. The planar retinaculum has a thickness in the range of 0.5 mm to 2 mm. A thumb tack extends through one of the smallest diameter apertures for removably securing a fractured bone segment to the retinaculum. The apertures consist of three groups of apertures including a first group of small diameter apertures, a second group of medium-size apertures, and a third group of large apertures. All of the apertures within each group have the same diameter.

The apertures are arranged in columns and transversely-oriented rows. Each row and each column comprise a repeating pattern of differently-sized apertures. The pattern comprises one aperture from the first group, followed by one aperture from the second group, followed by one aperture from the third group. Adjacent columns and adjacent rows are staggered by one aperture so that apertures from each group are aligned with each other along a diagonal line extending obliquely with respect to the columns and rows. The retinaculum may be used in conjunction with a bone plate made from the same material.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENTS

Figure 1:
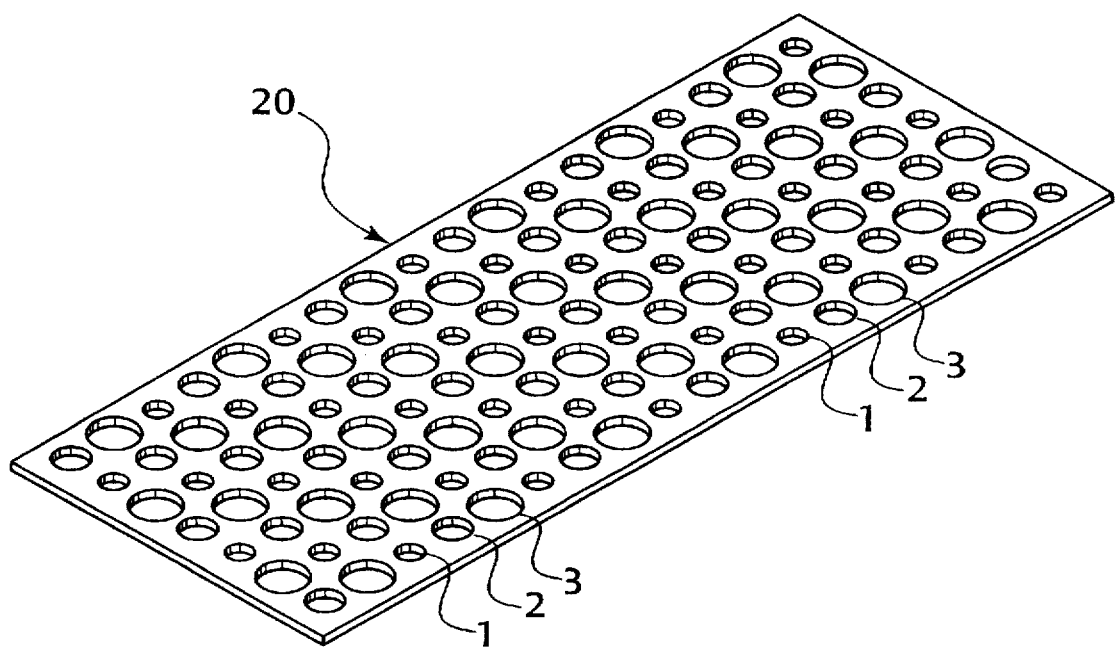
FIG. 1 is a front side elevational view of a retinaculum according to the invention with holes of three different diameters.
Figures 2, 3, 4:
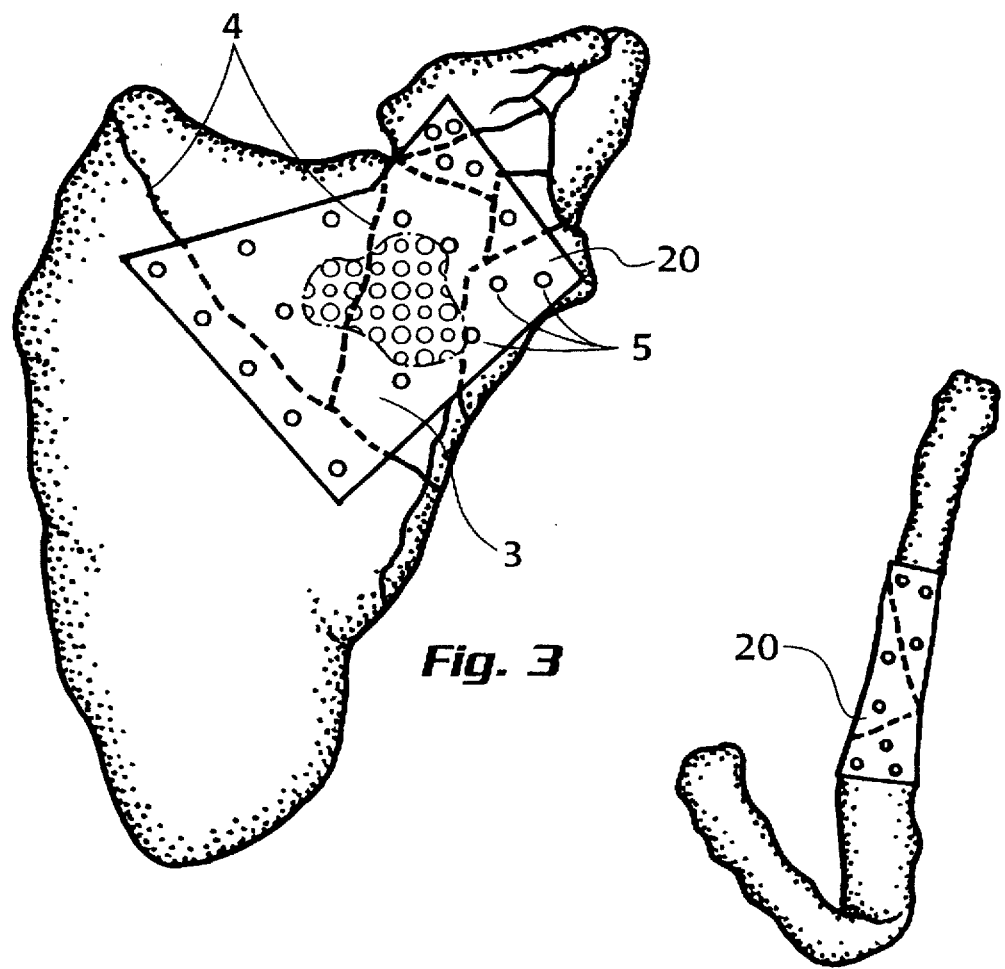
FIG. 2 shows the retinaculum in use on a comminuted fracture of the pseudarthroses of the clavicle.
FIG. 3 shows the retinaculum in use on a comminuted fracture of the glenoid and the central part of the scapula.
FIG. 4 shows the retinaculum in use on a comminuted fracture of a rib.

Referring now in detail to the drawings, and in particular FIG. 1, there is shown a retinaculum 20 according to the invention, which is formed as a thin plate or planar structure. Retinaculum 20 is made from titanium, steel or other known bio-compatible materials.

Retinaculum 20 has a series of holes or apertures 1, 2 and 3 extending therethrough which are arranged in rows and columns, for example. The apertures consist of three or more sets of holes with different diameters arranged in a "honeycomb structure". The holes have a diameter in the range of 2.0 mm to 6.5 mm. Retinaculum 20 has a thickness of 0.5 mm to 2 mm. The three holes with different diameters permit the use of screws or nails of different sizes. This is particularly advantageous for multi-fragmented and comminuted fractures.

Figure 5:
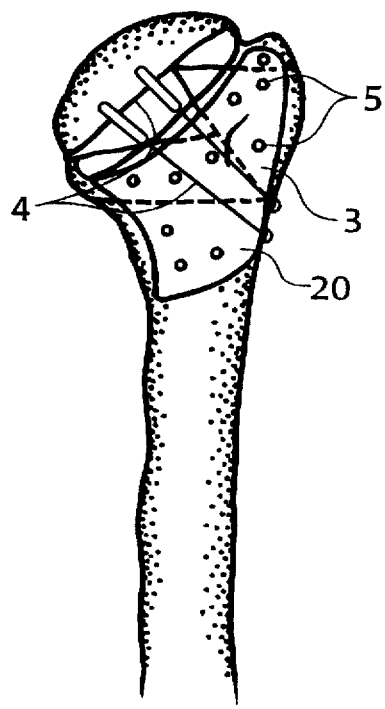
FIG. 5 shows the retinaculum in use on a multi-fragmented fracture of the humeral head and neck.
Figure 6:
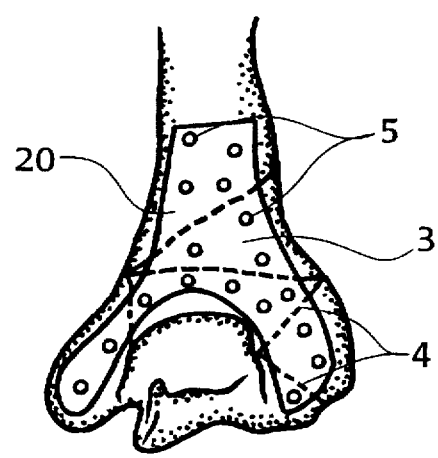
FIG. 6 shows the retinaculum in use on a comminuted fracture of the humeral disk.
Figure 7:
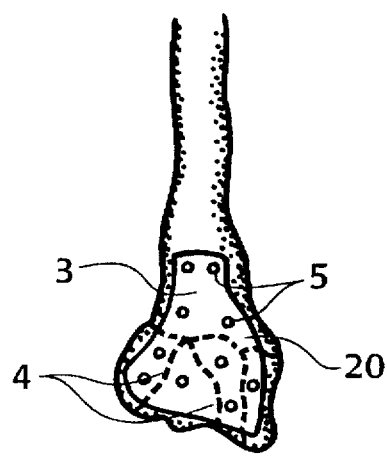
FIG. 7 shows the retinaculum in use on a multi-fragmented fracture of the distal epiphyses of the radius.
Figure 8:
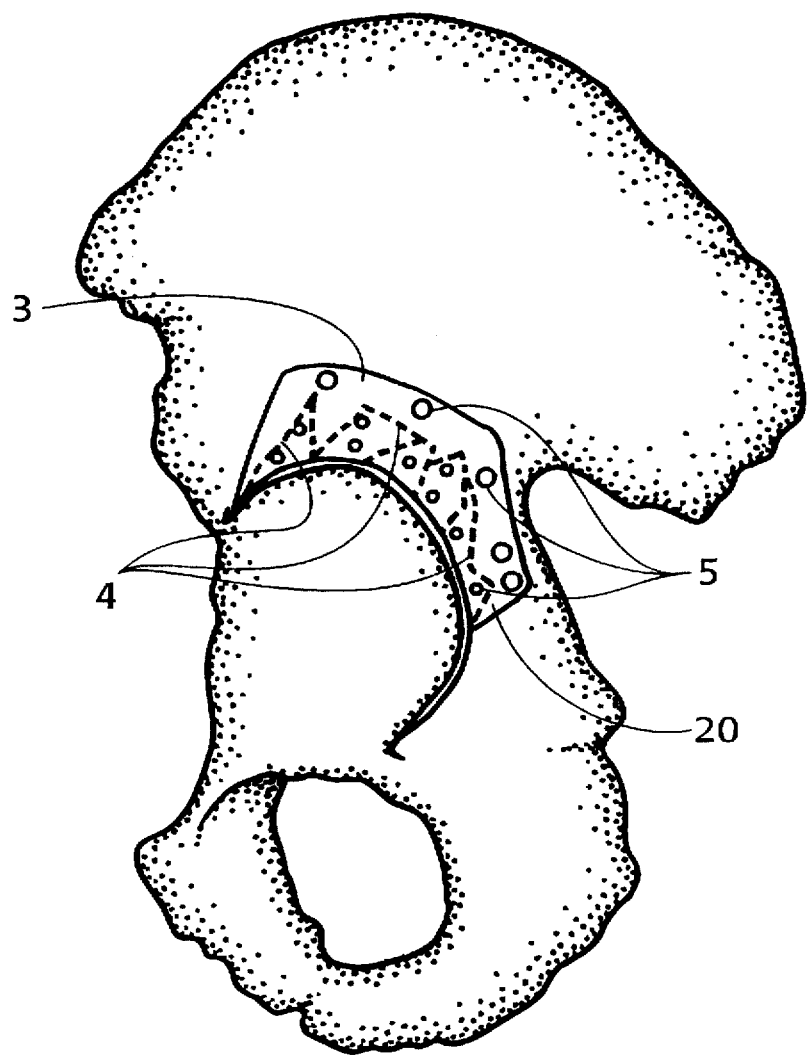
FIG. 8 shows the retinaculum in use on a multi-fragmented, comminuted fracture of the acetabular roof.
Figure 9:
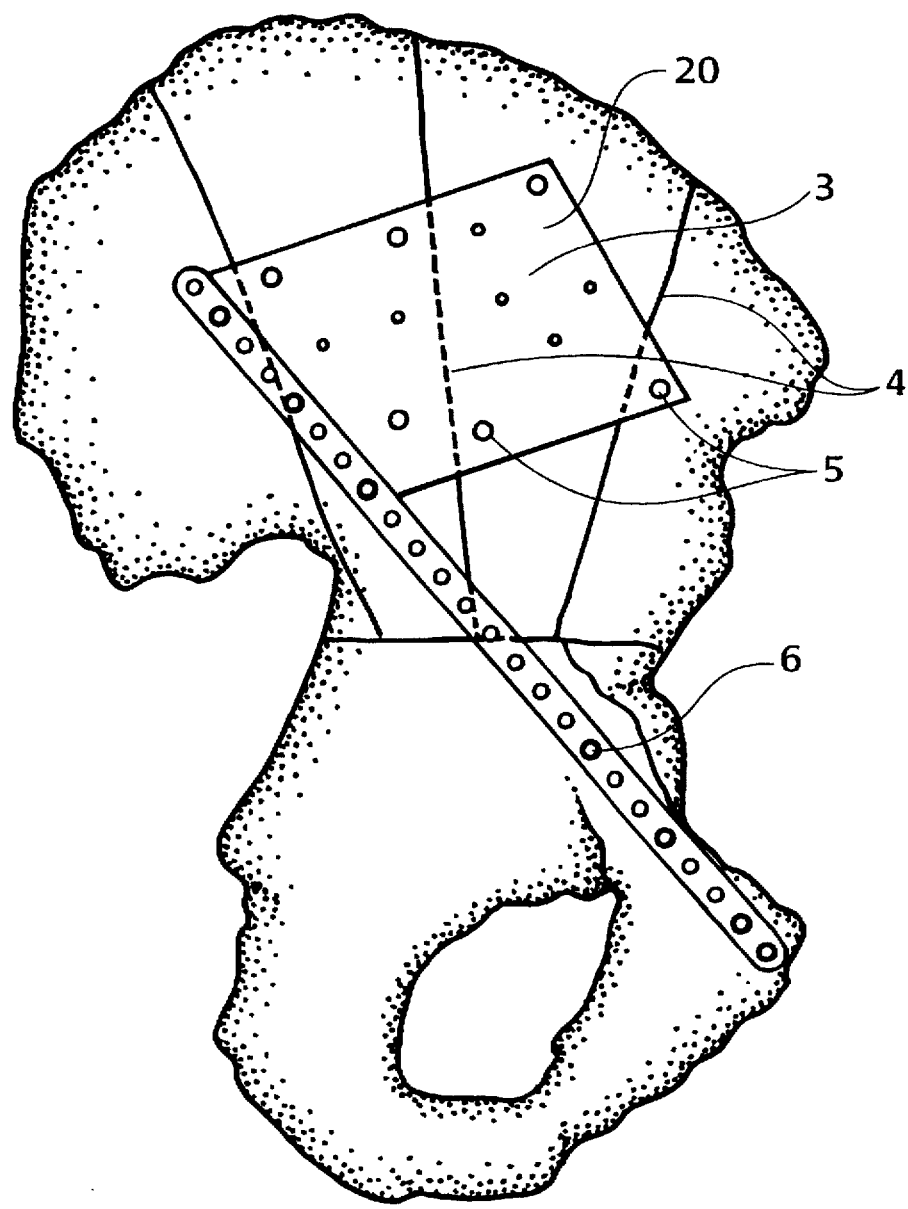
FIG. 9 shows the retinaculum in use on a multi-fragmented fracture where the acetabulum is subsequently connected with a plate.
Figure 10:
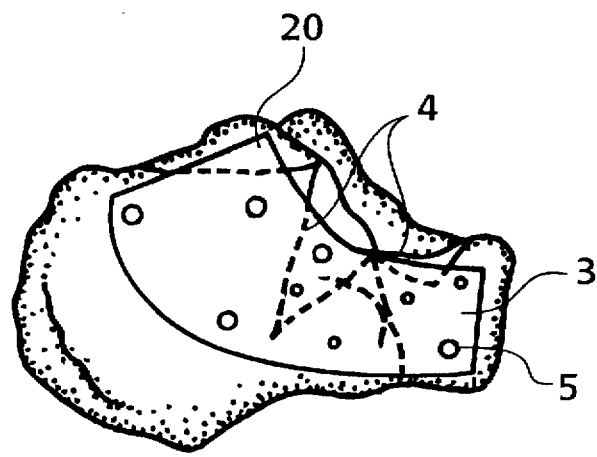
FIG. 10 shows the retinaculum in use on a multi-fragmented fracture of the heel.
Figure 11:
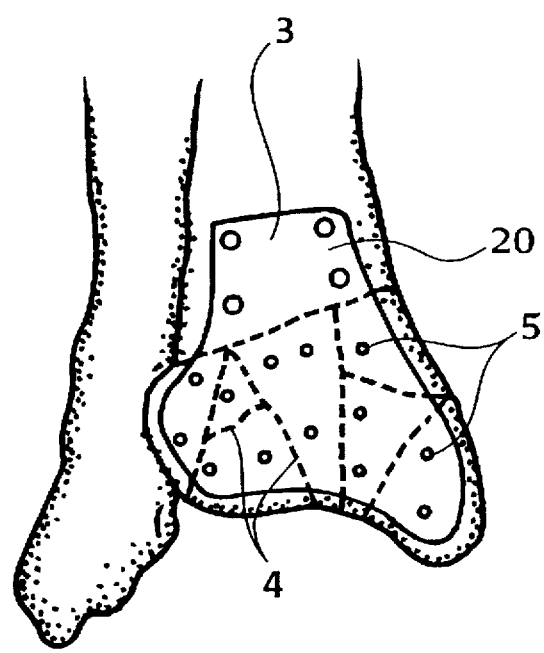
FIG. 11 shows the retinaculum in use on a comminuted fracture of the tibia.

The thickness of retinaculum 20 is selected based on the type of fracture. Various comminuted and multi-fragmented fractures 4 are shown in FIGS. 2–11. As can be seen, the shape and thickness of the retinaculum may be selected by the surgeon for a wide variety of applications. The variously-sized apertures 1, 2 and 3 allow different sized nails or tacks to be used depending on the size of the bone fragment to be secured. The apertures are arranged to provide a wide selection of fastening sites, i.e. apertures, for the surgeon. Another advantage of this invention is that the retinaculum can be combined with known plates 6 (see FIG. 9), provided that the plate and the retinaculum are made of the same material. FIGS. 5 and 11 show retinaculum 20 used in conjunction with bone screws.

The presence of small diameter holes allow temporary fastening with easily removable nails or thumb tacks 5. This allows the surgeon to operate with greater freedom and precision. Use of this retinaculum according to the invention represents an absolute innovation in orthopedic traumatology with undoubted advantages for setting bone fractures.

Accordingly, while only several embodiments of the present invention have been shown and described, it is obvious that many changes and modifications may be made thereunto without departing from the spirit and scope of the invention.

What is claimed is:

1. A device for securing comminuted fractured bone segments in place comprising:

a planar retinaculum having a plurality of apertures extending therethrough, said plurality of apertures consisting of three groups of apertures including a first group, a second group larger than said first group, and a third group larger than said second group, wherein all of the apertures within each group have the same diameter, wherein said plurality of apertures are arranged in columns and transversely-oriented rows along said retinaculum, and wherein each row and each column comprises a repeating pattern of differently sized apertures.

2. The device according to claim 1, comprising a thumb tack for extending through the apertures having the smallest diameter for removably securing a fractured bone segment to said retinaculum.

3. The device according to claim 1, wherein said pattern comprises one aperture from said first group, followed by one aperture from said second group followed by one aperture from said third group.

4. The device according to claim 3, wherein adjacent columns and adjacent rows are staggered by one aperture so that apertures from each group are aligned with each other along a diagonal line extending obliquely with respect to the columns and rows.

5. The device according to claim 1, comprising a bone plate for use in conjunction with said retinaculum.

6. The device according to claim 5, wherein said bone plate and said retinaculum are made from the same material.

7. The device according to claim 5, comprising a thumb tack for extending through the group of apertures having the smallest diameter for removable securing a fractured bone segment to said retinaculum.

* * * * *